(12) United States Patent
Santos et al.

(10) Patent No.: US 9,349,260 B2
(45) Date of Patent: May 24, 2016

(54) SENSOR DEVICE WITH ENHANCED LIGHT GUIDE VISUALIZATION AND RELATED METHODS

(71) Applicant: Rockwell Automation Technologies, Inc., Mayfield Heights, OH (US)

(72) Inventors: Roberto Santos, Hudson, MA (US); Frank L. Leard, Sudbury, MA (US)

(73) Assignee: ROCKWELL AUTOMATION TECHNOLOGIES, INC., Mayfield Heights, OH (US)

( * ) Notice: Subject to any disclaimer, the term of this patent is extended or adjusted under 35 U.S.C. 154(b) by 0 days.

(21) Appl. No.: 14/079,551

(22) Filed: Nov. 13, 2013

(65) Prior Publication Data

US 2015/0130626 A1    May 14, 2015

(51) Int. Cl.
| G08B 5/00 | (2006.01) |
| G08B 5/36 | (2006.01) |
| F21V 8/00 | (2006.01) |
| G01N 21/00 | (2006.01) |

(52) U.S. Cl.
CPC *G08B 5/36* (2013.01); *G01N 21/00* (2013.01); *G02B 6/0001* (2013.01)

(58) Field of Classification Search
CPC .. A61B 3/132; G02B 21/0012; G02B 21/082; G02B 21/0016; G02B 6/08; B02C 13/1835; D01H 1/02; E06B 11/08; F21S 8/026; F21V 14/02; F21V 21/04; G01B 11/00; G03B 1/56; G03B 21/32; G03B 27/46
USPC ............... 340/815.4, 815.43–815.44, 815.49, 340/815.53, 815.55–815.56, 815.73, 815.77
See application file for complete search history.

(56) References Cited

U.S. PATENT DOCUMENTS

| 5,713,533 | A | * | 2/1998 | Nordlof | B65H 23/042 226/42 |
| 5,813,070 | A | * | 9/1998 | Dittrich | E01D 15/133 14/2.4 |
| 5,947,578 | A | | 9/1999 | Ayres | |
| 6,095,669 | A | * | 8/2000 | Cho | 362/365 |
| 6,937,812 | B2 | | 8/2005 | Schladenhauffen et al. | |
| 6,958,694 | B1 | | 10/2005 | Shafiyan-Rad et al. | |

(Continued)

FOREIGN PATENT DOCUMENTS

| EP | 1632708 A2 | 3/2006 |
| EP | 2085800 A1 | 8/2009 |

OTHER PUBLICATIONS

Extended European Search Report, for Corresponding EP Application No. 14192995.0, 7 pages, Apr. 22, 2015.

*Primary Examiner* — Daniel Previl

(74) *Attorney, Agent, or Firm* — Viksnins Harris & Padys PLLP

(57) ABSTRACT

A sensing device comprises a sensor housing defined in part by two or more outer planes, a light guide including one or more legs, where the light guide defined in part by a vertical plane, and the light guide is an indicator for the sensing device. The light guide extends along a first portion and a second portion, where the first portion is disposed along at a first outer plane of the housing, the second portion is disposed along a second outer plane of the housing. The sensing device further includes a light source disposed adjacent to the light guide, and the light guide includes at least one slot therein. The light source is directed toward the slot, and a surface within the slot transmits light in multiple directions.

21 Claims, 8 Drawing Sheets

(56) References Cited

U.S. PATENT DOCUMENTS

| | | |
|---|---|---|
| 7,009,525 B1 | 3/2006 | Shafiyan-Rad et al. |
| 7,190,268 B1 | 3/2007 | Rad et al. |
| 8,421,037 B2 | 4/2013 | Leard |
| 8,480,246 B2 | 7/2013 | Leard |
| 8,989,612 B2 * | 3/2015 | Miyagawa ................ 399/81 |
| 2006/0225495 A1 * | 10/2006 | Tatsuno ..................... 73/149 |
| 2007/0036511 A1 * | 2/2007 | Lundquist et al. ........... 385/147 |
| 2007/0144991 A1 * | 6/2007 | Hansl ................ B65G 1/0407 211/121 |
| 2010/0063508 A1 * | 3/2010 | Borja ................ A61B 17/154 606/88 |
| 2011/0187353 A1 * | 8/2011 | Mizusaki et al. ........ 324/207.11 |
| 2013/0126666 A1 * | 5/2013 | Brown ..................... B60F 5/02 244/2 |
| 2013/0194776 A1 | 8/2013 | Santos et al. |
| 2013/0194778 A1 | 8/2013 | Santos et al. |

* cited by examiner

US 9,349,260 B2

SENSOR DEVICE WITH ENHANCED LIGHT GUIDE VISUALIZATION AND RELATED METHODS

TECHNICAL FIELD

The present invention relates to the field of sensors and, more particularly, to methods and devices for enhancing the visibility of sensor indicators.

TECHNICAL BACKGROUND

Industrial sensors are commonly used in a wide variety of applications and environments. Industrial sensors, such as proximity, mechanical switches, optical and photoelectric sensors, can be used to detect the presence or absence of targets on a conveyor belt, for example. Likewise, safety rated sensors can be used to prevent unauthorized or unintended access into a hazardous area, such as a safety interlock sensor that detects that a machinery guard door is closed before the machine operates. In addition, industrial sensors can be used to monitor various components of process machinery.

Industrial sensors often use one or more light sources that serve as indicators to convey a status signal, such as power, output, or margin, to an end user during set-up and operation. Light from the light source is often conveyed through a light pipe or similar optical structure serving to guide the light to the external environment. The light source is often colored or projected through a colored lens to emit colored light, often green, yellow, orange, or red. The visibility of these light-guide-coupled light sources is usually good when viewed head-on by the end-user. However, the visibility of these light-guide-coupled light sources is often poor when viewed from a large off-center angle, such as when viewed by the end-user from the side. The visibility of these light sources is often reduced as the distance to the exterior environment increases.

Various solutions have been tried to address poor sensor indicator visibility from viewing angles other than head-on, such as selecting brighter (and possibly larger) light source components, increasing the electrical current supplied to the light source, moving the light source closer to the exterior surface, and using physical optical structures such as prisms, or light pipes. Although these methods can increase indicator visibility from directions other than head-on, they include various drawbacks, such as more expensive parts, additional part processing, increased electric load on a base circuit, presenting dirt traps that reduce product hygiene, and increased housing size to accommodate larger parts or additional structures.

What is needed is a device or method that preserves the head-on visibility of sensor indicators while simultaneously enhancing the visibility from viewing angles other than head-on, and overcomes the above-discussed drawbacks.

SUMMARY

A sensing device comprises a sensor housing defined in part by two or more outer planes, a light guide including one or more legs, where the light guide is defined in part by a vertical plane, and the light guide is an indicator for the sensing device. The light guide extends along a first portion and a second portion, where the first portion is disposed along a first outer plane of the housing, the second portion is disposed along a second outer plane of the housing. The sensing device further includes a light source disposed adjacent to the light guide, and the light guide includes at least one slot therein. The slot of the light guide has an angle of about 18-24 degrees relative to the longitudinal axis of the light guide. The light source is directed toward the slot, and a surface within the slot transmits light in multiple directions; it does not bend all of the light. A portion of the light is transmitted along the first portion and a portion of the light is transmitted along the second portion.

In one or more embodiments, a method of providing indication for a sensing device is provided herein. The method includes sensing an operational status at a sensor circuit, generating a signal at the sensor circuit based on the sensed operational status, utilizing the signal to activate a light source, transmitting light from the light source to a light guide through a first portion to a slotted portion, the slotted portion having a planar surface disposed at an angle 18-24 degrees relative to a longitudinal axis of the light guide. The light guide can include any of the embodiments discussed and/or shown herein.

Other embodiments, aspects, features, objectives, and advantages of the present invention will be understood and appreciated upon a full reading of the detailed description and the claims that follow.

BRIEF DESCRIPTION OF THE DRAWINGS

Embodiments of the invention are disclosed with reference to the accompanying drawings and are for illustrative purposes only. The invention is not limited in its application to the details of construction or the arrangements of components illustrated in the drawings. The invention is capable of other embodiments or of being practiced or carried out in various other ways. Like reference numerals are used to indicate like components. In the drawings.

DETAILED DESCRIPTION

The following detailed description refers to the accompanying drawings that show, by way of illustration, specific details and embodiments in which the invention may be practiced. These embodiments, which are also referred to herein as "examples," or "options" are described in sufficient detail to enable those skilled in the art to practice the invention.

A light guide for a control device and related methods are provided herein. The light guide allows for enhanced viewing of indicators from multiple sides of a housing for the control device. For example the control device includes a sensor device with a housing and indicator, and the indicator can be viewed from both the top and sides and any angle in between without using a raised structure. The novel light guide allows for light to be dispersed in directions up to 270° around the housing.

In one or more embodiments, the control device, such as the sensing device, includes a sensor housing defined in part by two or more outer planes. The device further includes a light guide including one or more legs, the light guide defined in part by a vertical plane, and the light guide is an indicator for the sensing device. The light guide extends along a first portion and a second portion, where the first portion is disposed along at a first outer plane of the housing, and the second portion is disposed along a second outer plane of the housing. The device further includes a light source disposed adjacent to the light guide, where the light guide includes at least one slot therein, and the slot has an angle of about 18-24 degrees relative to the vertical plane of the light guide. The light source is directed toward the slot, and a surface within the slot transmits light in multiple directions. A portion of the light transmitted along the first portion and a portion of the light transmitted along the second portion.

Figure 1:
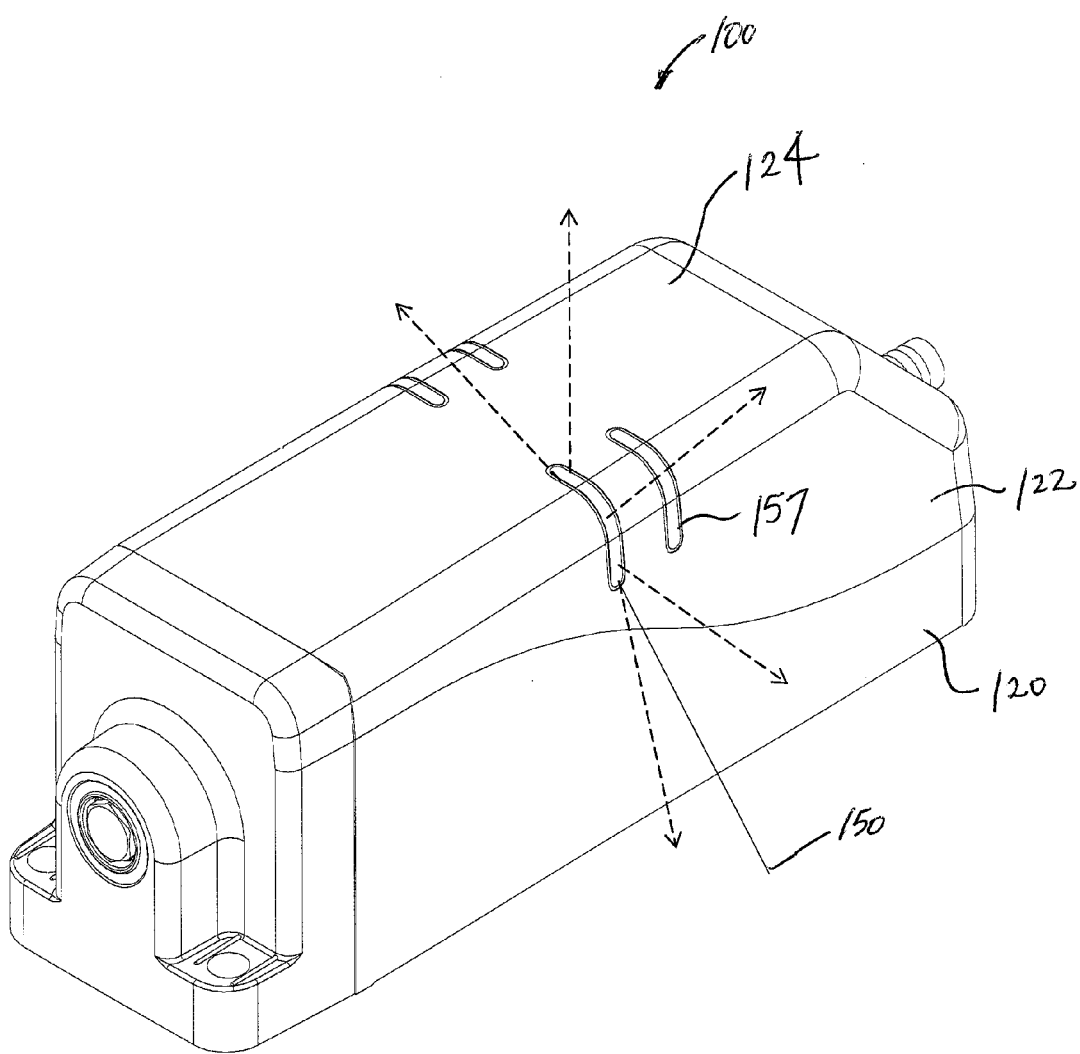
FIG. 1 illustrates an isometric view of a sensing device as constructed in accordance with one or more embodiments.
Figure 2:
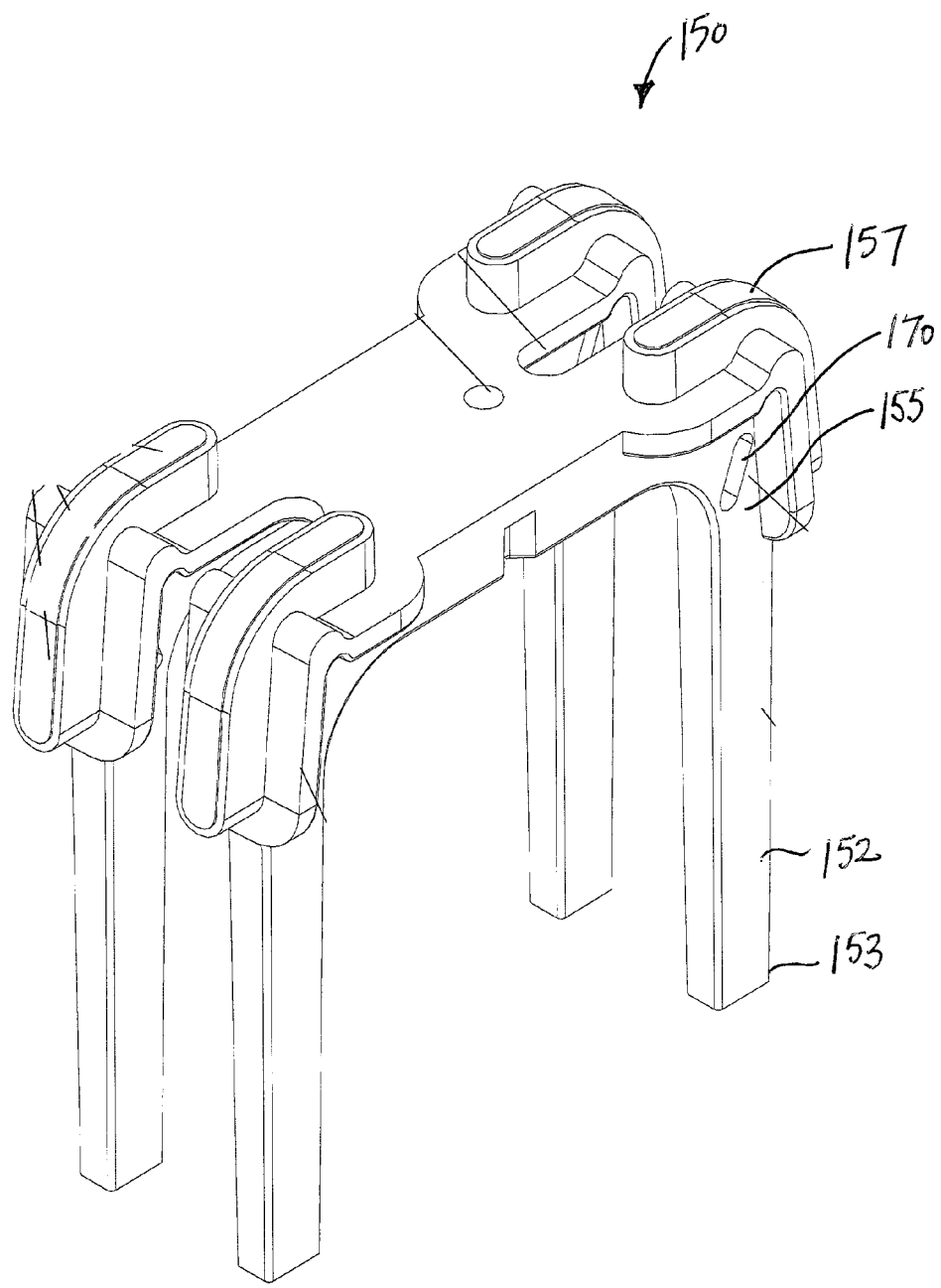
FIG. 2 illustrates an isometric view of the slotted light guide as constructed in accordance with one or more embodiments.
Figure 3:
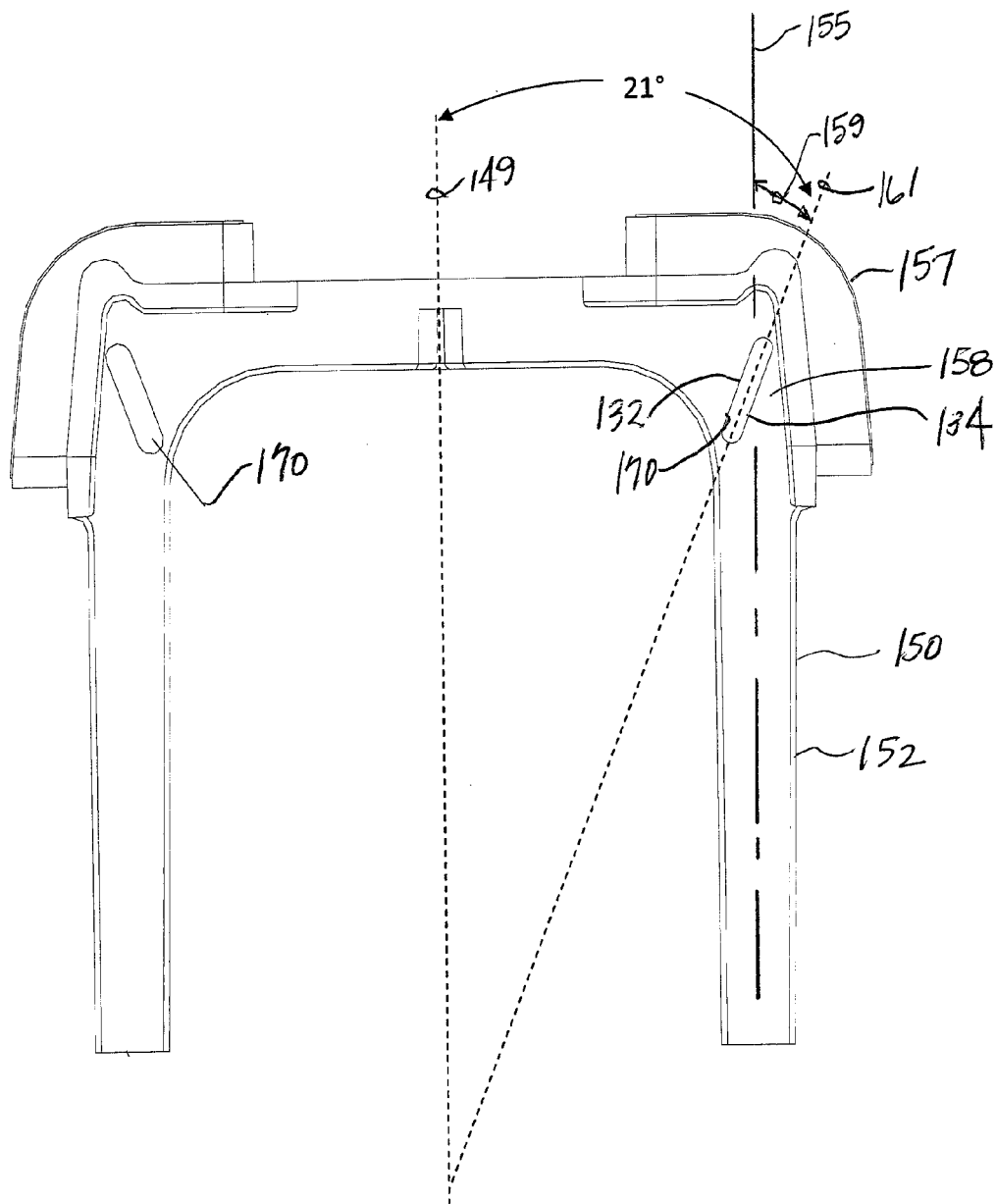
FIG. 3 illustrates a front view of the slotted light guide as constructed in accordance with one or more embodiments.
Figure 4:
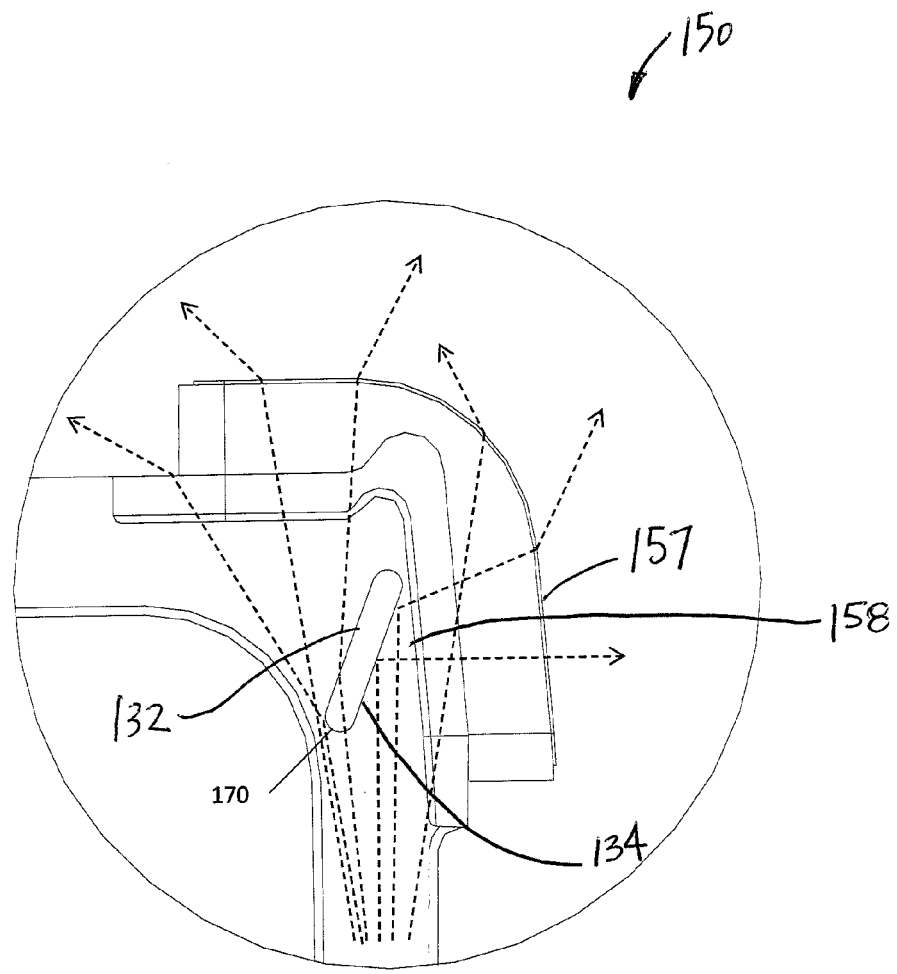
FIG. 4 illustrates a detail of the slot structure in the light guide as constructed in accordance with one or more embodiments.
Figure 6:
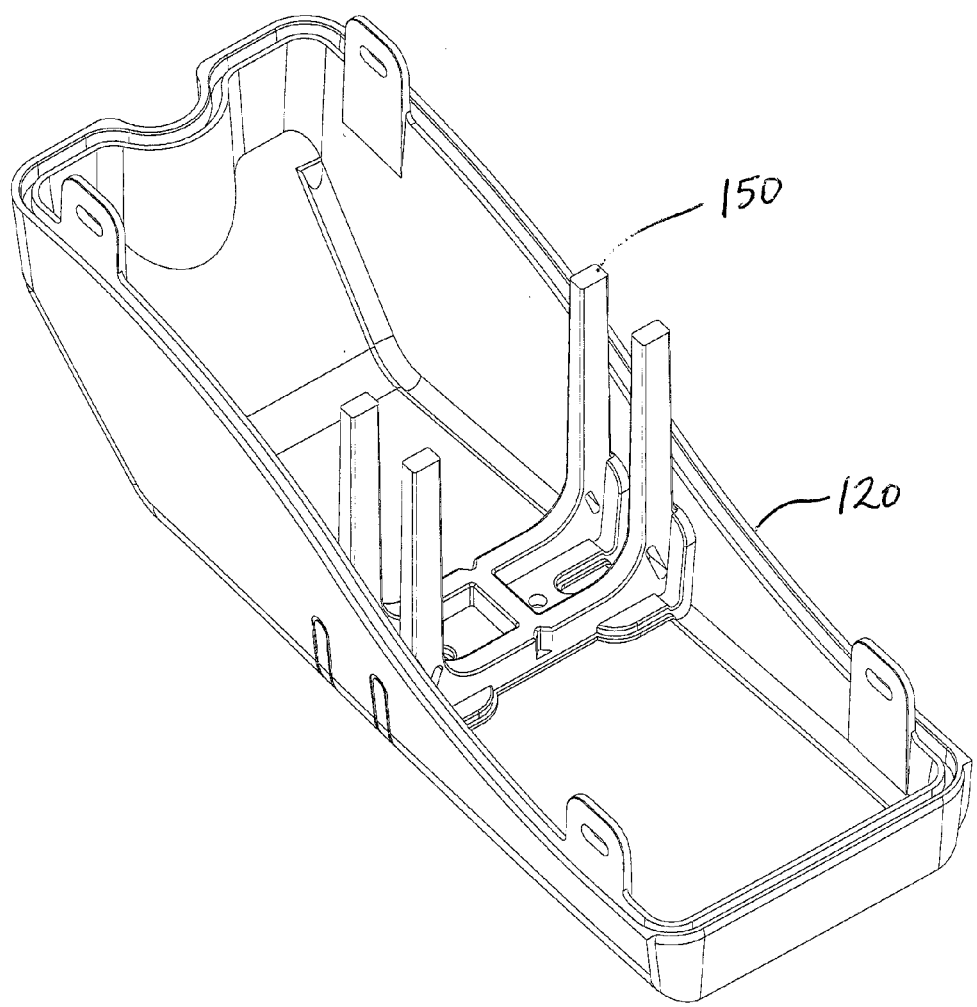
FIG. 6 illustrates a bottom perspective view of the sensor housing as constructed in accordance with one or more embodiments.
Figure 7:
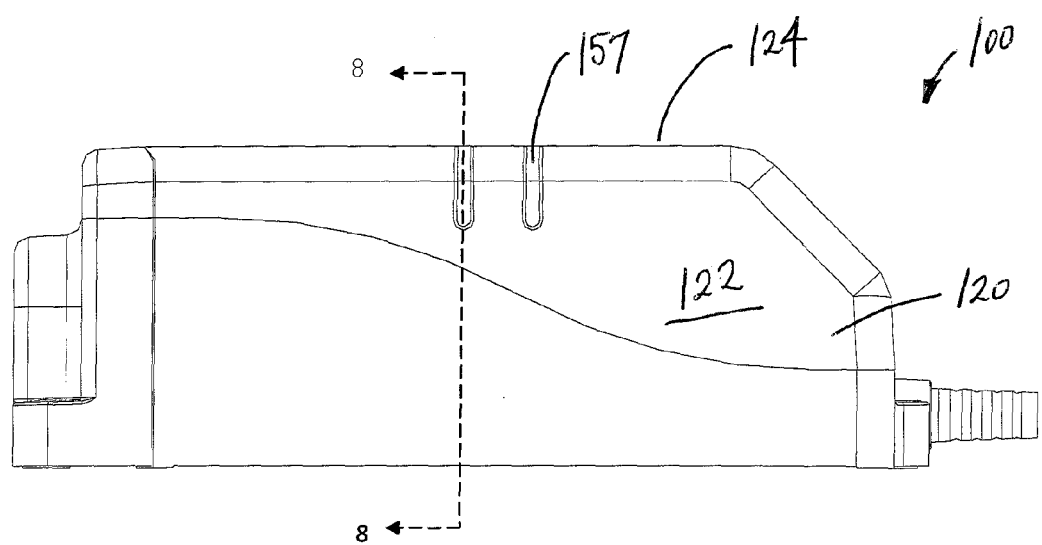
FIG. 7 illustrates a side view of the sensing device as constructed in accordance with one or more embodiments.

FIGS. 1-3 illustrate one or more embodiments of a sensing device 100, which includes a light guide 150 therein which has an indicating ability, and forms an indicator which can be viewed external to the device. The sensing device 100 includes a housing 120 defined in part by a first outer plane 122 and a second outer plane 124. The housing 120 is configured to at least partially enclose a light guide, light source, and electronics. FIG. 6 illustrates a bottom view of a housing 120 with the light guide 150 therein. The light source 190 (FIG. 8) is disposed adjacent to the light guide 150, in one or more embodiments, and provides light to illuminate the indicator to provide an indication based on the sensing of an event at the sensor 100. The sensing device 100 can include various types of sensing circuits for providing an output to energize the light source 190 (FIG. 8) when desired conditions are met. Such sensing circuits are commonly found, for example, in proximity sensors and photosensors.

Figure 8:
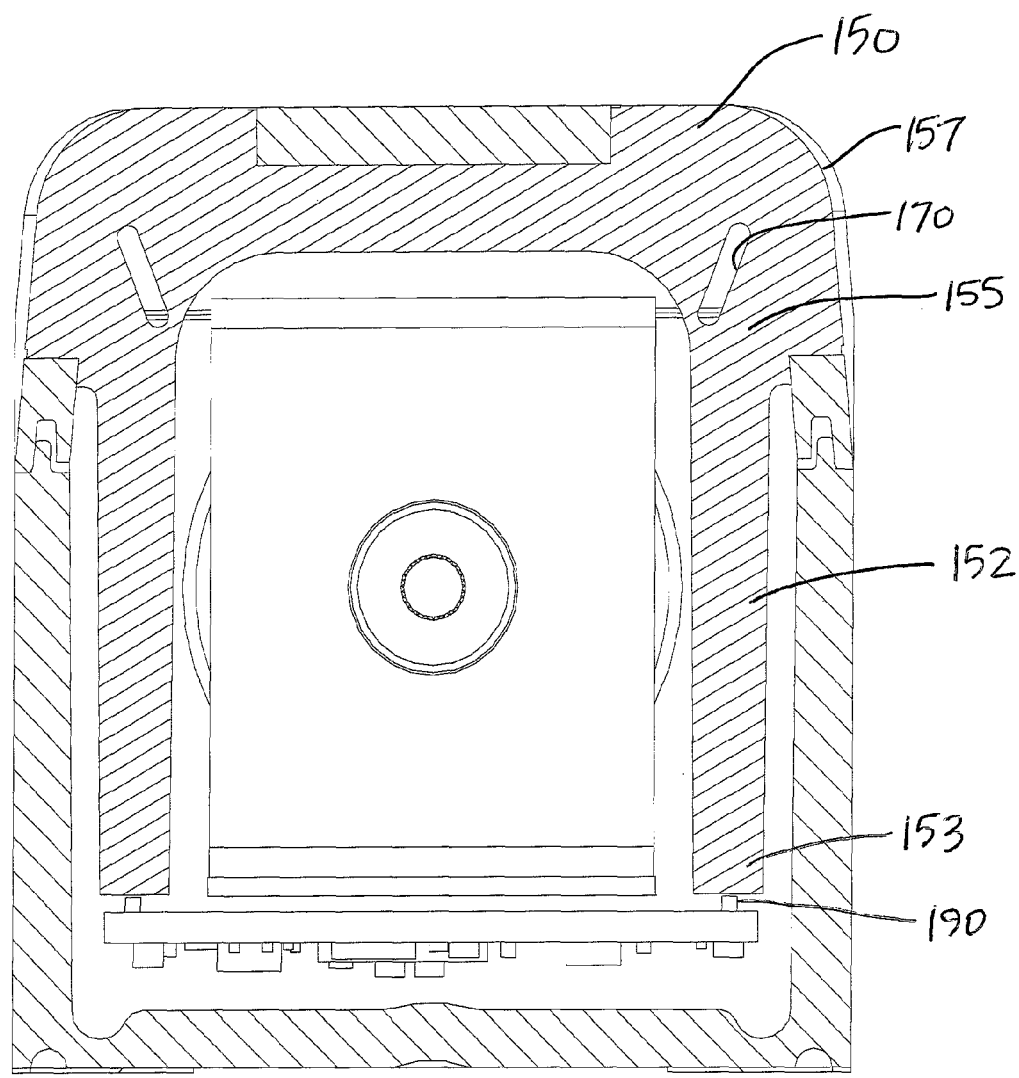
FIG. 8 illustrates a cross-section view taken along line 8-8 shown in FIG. 7 as constructed in accordance with one or more embodiments.

FIG. 2 illustrates a light guide 150 in accordance with one or more embodiments. The light guide 150 includes a first portion 152 which is extends from a first end portion 153 to a second end portion 158 (FIG. 3). In one or more embodiments, the first end portion 153 is disposed directly adjacent to the light source 190 (FIG. 8). The first portion 152 is defined by a longitudinal axis 155 (FIG. 3).

Disposed near the second end portion 155 is the external indicator 157 which extends along two different outer planes of the housing 120. In one or more embodiments, the external indicator is sized relative to the housing such that the light guide is flush with the outer portion of the housing, thereby preventing materials from the environment from being trapped within the light guide, or between the light guide and the housing. In one or embodiments, the external indicator 157 has an outer textured surface for additional distribution of light.

In one or more embodiments, the light guide 150 includes one or more slots 170 formed within the light guide 150. The slot 170 is disposed along a light path and assists in dispersing the light from traveling along in one direction to traveling in multiple directions. For example, in one or more embodiments, the slot 170 is a scatter slot where the light is not entirely bent by the slot, it is scattered by the slot into multiple directions so that the light is visible from multiple sides of the housing.

The slot 170 is defined in part by a slot longitudinal axis 161. In one or more embodiments, the slot 170 has a linear shape along the axis 161, and/or includes rounded ends. In one or more embodiments, the slot 170 includes an interior portion 132 and an exterior portion 134, where the exterior portion 134 is disposed toward the first plane 122 of the exterior portion of the housing, and the interior portion 132 is disposed toward the second outer plane 124 of the housing. In one or more embodiments, the slot 170 is linear and not curved, for example, around a corner. In one or more embodiments, the first side 122 forms a top of the housing and the second plane 124 forms a side of the housing.

Referring to FIG. 3, in one or more embodiments, the slot 170, or optionally plurality of slots, is disposed at an oblique angle relative to the incoming light. For example, the slot 170 is disposed at an angle relative to the longitudinal axis 155, and the light from the light source travels along the longitudinal axis 155. In one or more embodiments, the angle 159 between the longitudinal axis 155 of the light guide first portion and a slot longitudinal axis 161 is 18-24 degrees. In one or more embodiments, the angle 159 is 21 degrees. In one or more embodiments, the light guide 150 is defined in part by a vertical plane 149, such as a central vertical plane.

In one or more embodiments, the slot axis 161 is disposed at an angle of the central vertical plane axis of 18-24 degrees, and in one embodiment 21 degrees. In one or more embodiments, the slot 170 is oriented such that the exterior portion 134 of the slot is angled toward the light source, and the interior portion 132 is disposed away from the light source and toward an upper portion 124 of the housing. The light source is directed toward the slot, such as the exterior portion 134 of the slot 170, and a surface within the slot transmits light in multiple directions; it does not bend all of the light. A portion of the light is transmitted along the first portion and a portion of the light is transmitted along the second portion. The surface of the slot is optionally textured, for example, to a depth of 0.001-0.003 in.

Figure 5:
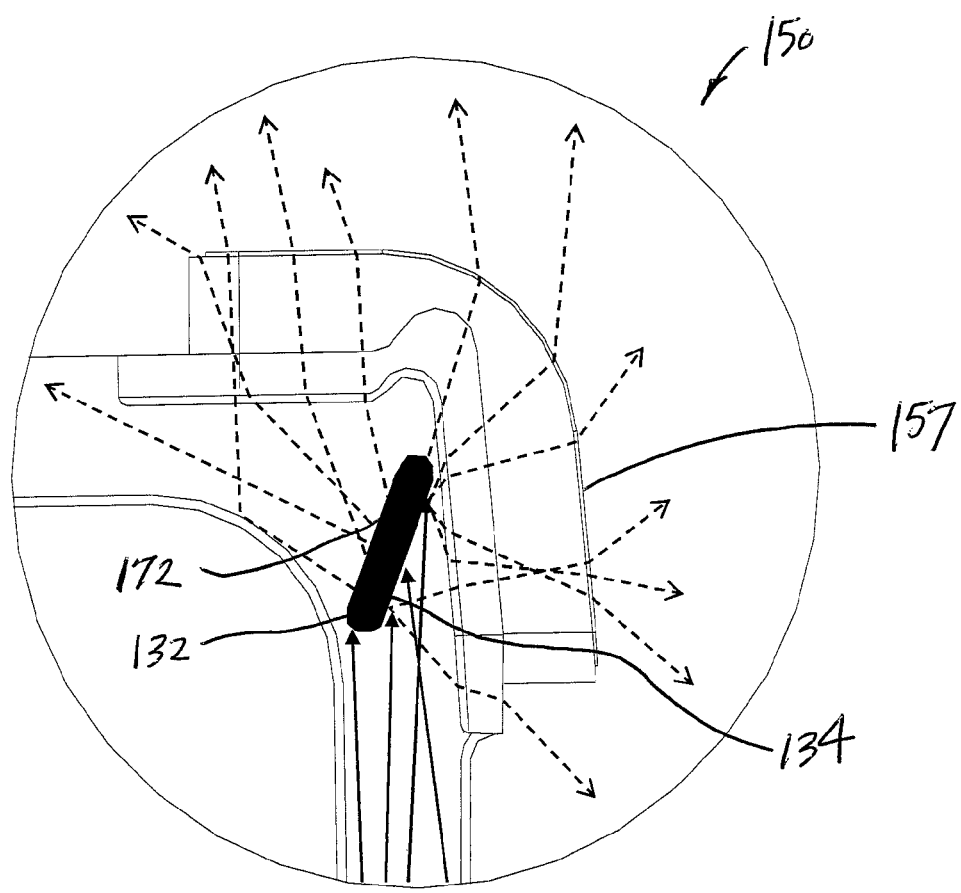
FIG. 5 illustrates the light guide assembly as constructed in accordance with one or more embodiments.

In one or more embodiments, the slot 170 includes a fluorophore therein, as shown in FIG. 5. In one or more embodiments, the slot 170 is coated with fluorophores. In one or more embodiments, a plug 172 is disposed in the slot 170. In one or more embodiments, the plug 172 includes fluorophores, such as a coating or is dispersed within the plug 172. The slot 170 can include the oblique angle as discussed above. In one or more embodiments, the slot 170 is angled where the transmitted light from the light source approaches an interior portion 132 of the slot initially, and exits an exterior portion 134 of the slot. In one or more embodiments, the slot 170 is angled where the transmitted light from the light source approaches an exterior portion 134 of the slot initially, and exits an interior portion 132 of the slot.

In one or more embodiments, the light guide 150 has four light guides in one structure, although it is possible to have any number. Angled slots are cut into each light guide at a 18-24° angle, or in one or more embodiments a 21° angle with respect to a vertical centerline, creating a hollow void all the way through the four legs of the light guide. In one or more embodiments, the interior of the angled slots are textured, such as per AMT 9120, for example textured to a depth of about 0.001-0.003 inches, or in another embodiment 0.002 inches, to allow for scattering of the light rays. When light from the light source enters the bottom of the light guide, which in one or more embodiments is polished to an SPI-A3 or better finish, it hits the surface of the angled slot and a portion of the light scatters out the side of the indicator while the remaining portion exits out the top. Combined with optional large corner radii that help to further refract the light, there is a significant improvement in visibility from the sides and at high angles.

In one or more embodiments, the exterior surfaces of the light guide are textured, such as per AMT 9120, in order to create a more diffuse and uniform illumination when viewed by the end-user. The long legs of the light guide are polished to an SPI-A3 or better finish to promote total internal reflection.

In one or more embodiments, the light guide 150 is formed of acrylic (PMMA), but can also be made of other transparent polymers such as polycarbonate or styrene, for example by injection molding. Other materials such as glass may also be possible.

Referring to FIG. 5, in another embodiment, a remote phosphor could be used. The improvement would be to create a transparent plug that would be either coated with a fluorophore (a particle or set of particles that fluoresce upon excitation by a higher energy photon) or would encapsulate the fluorophore and insert it into the open slots. The fluorophore can be any one of a number of fluorescent materials including phosphors, nano-phosphors, quantum dots, and/or plasmonic structures. The light source would then become a blue LED, OLED, UV LED, blue laser diode, or a UV laser diode (collectively called LED). When light from the blue LED hits the fluorophore, the fluorophore absorbs the light received from the light source and, upon absorption, the wavelength of the light is both shifted along the electromagnetic spectrum from a higher energy, shorter wavelength to a lower energy, longer wavelength and scattered in many directions to increase the visibility of the light to the human eye from various observation directions. So, although the light emitted by the LED is blue, after it hits the fluorophore it will change to another color such as red, yellow, or green for example. Alternatively, the surfaces of the slot can be coated with the fluorophore instead of using a plug.

In one or more embodiments, the light guide is overmolded into the sensor cover, thereby creating a hermetic seal and providing a rigid, permanent attachment without the need for adhesives or screws. The flanges are optionally provided that surround the light guide increase the surface contact area with the overmolded cover to create a fluid-tight seal around the light guide's irregular geometry. The overmold material must be compatible with the light guide material. In this case, the acrylic (PMMA) light guide is overmolded with an ABS plastic, but other compatible polymers can also be used.

In one or more embodiments, a key is provided. For example, a hole in the top surface of the light guide serves as a means of keying the light pipes in the injection molding tool prior to overmolding with the ABS plastic to ensure proper installation. A gap between the light guide legs allows for some flexibility in misalignment when inserting the light guide into the overmolding tool. Although this particular design uses overmolding to assemble the light guide to the cover, other methods of joining the two components can also be used such as adhesive bonding, welding, fasteners, etc.

In one or more embodiments, a method of providing indication for a sensing device is provided herein. The method includes sensing an operational status at a sensor circuit, generating a signal at the sensor circuit based on the sensed operational status, utilizing the signal to activate a light source, transmitting light from the light source to a light guide through a first portion to a slotted portion, the slotted portion having a planar surface disposed at an angle 18-24 degrees relative to a vertical axis of the light guide. The light guide can include any of the embodiments discussed and/or shown herein.

The method further includes transmitting light to a first plane of a housing of the sensing device, directing light away from the vertical axis toward a second plane of the housing of the sensing device, and emitting light from the first plane and the second plane of the housing.

Several variations include mounting a plug within the slotted portion, or mounting a fluorophore plug within the slotted portion, or coating the slotted portion with a fluorophore. In one or more embodiments, the method further includes transmitting blue light into light guide and emitting a light other than blue light.

Although the above description discloses in at least some embodiments sensors for use in industrial controls, such as proximity and photoelectric sensors, it should be understood that other non-industrial and industrial sensing and indicating products can also be included, for example, light curtains, safety products, PLC's, motor drives, Through-Beam sensors, Transceiver sensors, Color Contrast sensors, Time-Of-Flight sensors, and stack lights.

The above Detailed Description is intended to be illustrative, and not restrictive. The various embodiments are not necessarily mutually exclusive, as some embodiments can be combined with one or more other embodiments to form new embodiments. For example, the above-described embodiments (and/or aspects thereof) embodiments may be combined, utilized and derived therefrom, such that structural and logical substitutions and changes may be made without departing from the scope of this disclosure. Such embodiments of the inventive subject matter may be referred to herein, individually and/or collectively, by the term "invention" merely for convenience and without intending to voluntarily limit the scope of this application to any single invention or inventive concept if more than one is in fact disclosed. Many other embodiments will be apparent to those of skill in the art upon reviewing the above description. The scope of the invention should, therefore, be determined with reference to the appended claims, along with the full scope of equivalents to which such claims are entitled.

The methods described herein do not have to be executed in the order described, or in any particular order, unless it is otherwise specified that a particular order is required. Moreover, unless otherwise specified, various activities described with respect to the methods identified herein can be executed in repetitive, simultaneous, serial, or parallel fashion.

The terms "a" or "an" are used, as is common in patent documents, to include one or more than one. The term "or" is used to refer to a nonexclusive or, unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring the abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment with each embodiment being combinable with each other embodiment.

We claim:

1. A sensing device comprising:
   a sensor housing defined in part by two or more outer planes;
   a light guide including one or more legs, the light guide defined in part by a vertical plane, and the light guide is an indicator for the sensing device;
   the light guide extending along a first portion and a second portion, where the first portion is disposed along at a first outer plane of the housing, the second portion is disposed along a second outer plane of the housing;
   a light source disposed adjacent to the first portion of the light guide;
   the light guide including at least one slot therein, the slot having a slot axis, the slot having an oblique angle of the slot axis relative to a longitudinal axis of the first portion of the light guide; and
   the light source directed toward the slot and a surface within the slot transmits light in multiple directions, a portion of the light transmitted along the first portion and a portion of the light transmitted along the second portion.

2. The sensing device as recited in claim 1, further comprising a plug disposed within the at least one slot, and the plug omni-directionally scatters light from the light source.

3. The sensing device as recited in claim 2, wherein the plug includes a fluorophore.

4. The sensing device as recited in claim 1, wherein a surface of the slot is coated with a fluorophore.

5. The sensing device as recited in claim 1, wherein the at least one slot is disposed at an angle of 18-24 degrees relative to the longitudinal axis.

6. The sensing device as recited in claim 1, wherein the at least one slot is disposed at an angle of 21 degrees relative to the longitudinal axis.

7. The sensing device as recited in claim 1, wherein the at least one slot has rounded ends.

8. The sensing device as recited in claim 1, wherein each of the slots have a textured surface, wherein the textured surface allows for scattering of light rays from the light source in several directions.

9. The sensing device as recited in claim 1, wherein the light source is one or more of a blue or UV light source.

10. The sensing device as recited in claim 1, wherein the slot creates a hollow void all way through the light guide.

11. A sensing device comprising:
    a sensor housing defined in part by two or more outer planes;
    at least one indicator within the sensor housing, the at least one indicator disposed on two or more outer planes of the housing;
    a light guide extending along a first portion and a second portion including two or more legs, the two or more legs having a longitudinal axis;
    a light source disposed adjacent to the light guide;
    the light guide including at least two slots therein;
    fluorophores disposed within the at least two slots; and
    the light source directed toward the at least two slots and a surface within the at least two slots transmits light in multiple directions, a portion of the light transmitted along a first portion of the light guide and a second portion of the light transmitted along the second portion of the light guide.

12. The sensing device as recited in claim 11, wherein the at least two slots have rounded ends.

13. The sensing device as recited in claim 11, wherein the light guide includes two or more legs, the two or more legs having a longitudinal axis, the slots disposed at an oblique angle relative to the longitudinal axis.

14. The sensing device as recited in claim 11, wherein each of the slots have a textured surface, wherein the textured surface allows for scattering of light rays from the light source in several directions.

15. The sensing device as recited in claim 11, wherein the light source is one or more of a blue or UV light source.

16. A method of providing indication for a sensing device, the method comprising:
    sensing an operational status at a sensor circuit;
    generating a signal at the sensor circuit based on the sensed operational status;
    utilizing the signal to activate a light source;
    transmitting light from the light source to a light guide through a first portion to a slotted portion, the slotted portion having a planar surface disposed at an angle 18-24 degrees relative to a longitudinal axis of the first portion;
    transmitting light to a first plane of a housing of the sensing device via the first portion;
    directing light away from the longitudinal axis toward a second plane of the housing of the sensing device; and
    emitting light from the first plane and the second plane of the housing.

17. The method as recited in claim 16, further comprising mounting a plug within the slotted portion.

18. The method as recited in claim 17, wherein mounting a plug includes mounting a fluorophore plug within the slotted portion.

19. The method as recited in claim 17, further comprising coating the slotted portion with a fluorophore.

20. The method as recited in claim 16, further comprising transmitting blue light into light guide and emitting a light other than blue light.

21. The method as recited in claim 16, further comprising transmitting light from the light source through the first portion to the slotted portion, wherein light is scattered by the slotted portion into multiple directions.

* * * * *